United States Patent
Svejkovsky et al.

(10) Patent No.: US 6,461,355 B2
(45) Date of Patent: *Oct. 8, 2002

(54) INSULATED ELECTRODE AND METHOD OF ASSEMBLY

(75) Inventors: Ronald D. Svejkovsky, Minnetona, MN (US); Randy L. Morningstar, Brooklyn Park, MN (US); Steven J. Ferry, Shorewood, MN (US); William M. Klatt, St. Louis Park, MN (US); John W. Westrum, Jr., Prior Lake, MN (US)

(73) Assignee: AMS Research Corporation, Minnetonka, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/323,168

(22) Filed: May 27, 1999

(65) Prior Publication Data

US 2002/0049440 A1 Apr. 25, 2002

(51) Int. Cl.⁷ ................................................ A61B 17/17
(52) U.S. Cl. ........................................ 606/41; 128/898
(58) Field of Search ............................ 128/898; 606/41, 606/45–59; 29/882, 611, 613, 825, 855, 856

(56) References Cited

U.S. PATENT DOCUMENTS

| | | | |
|---|---|---|---|
| 3,138,859 A | 6/1964 | Edwards | |
| 4,417,394 A | * 11/1983 | Moody et al. | 29/882 |
| 4,573,251 A | * 3/1986 | Hillyard | 29/235 |
| 5,658,280 A | 8/1997 | Issa | |
| 5,702,387 A | 12/1997 | Arts et al. | |
| 5,749,870 A | 5/1998 | Gloth et al. | |
| 5,810,764 A | 9/1998 | Eggers et al. | |
| 5,843,019 A | 12/1998 | Eggers et al. | |
| 5,845,396 A | 12/1998 | Altman et al. | |
| 5,846,355 A | 12/1998 | Spencer et al. | |

FOREIGN PATENT DOCUMENTS

| | | |
|---|---|---|
| CH | 684157 A5 | 7/1997 |
| EP | 0 154 193 A1 | 9/1985 |
| WO | WO 96/37156 A1 | 11/1996 |

* cited by examiner

Primary Examiner—Rosiland S. Kearney
(74) Attorney, Agent, or Firm—Jeffrey J. Hohenshell

(57) ABSTRACT

A design and method of manufacture is disclosed for an insulated electrode used during surgical procedures. The electrode includes a durable electrical insulation element that can withstand the range of temperatures generated during an electrosurgical procedure. Such insulation characteristics include resistance to meltback and manufacturability to ensure the device is biocompatible and non-toxic so as to prevent adverse reactions in both patients and users of the device. The insulated electrode further includes properties that reduce the incidence of scope damage caused by the intensity of heat generated during the cutting and coagulation cycles.

20 Claims, 4 Drawing Sheets

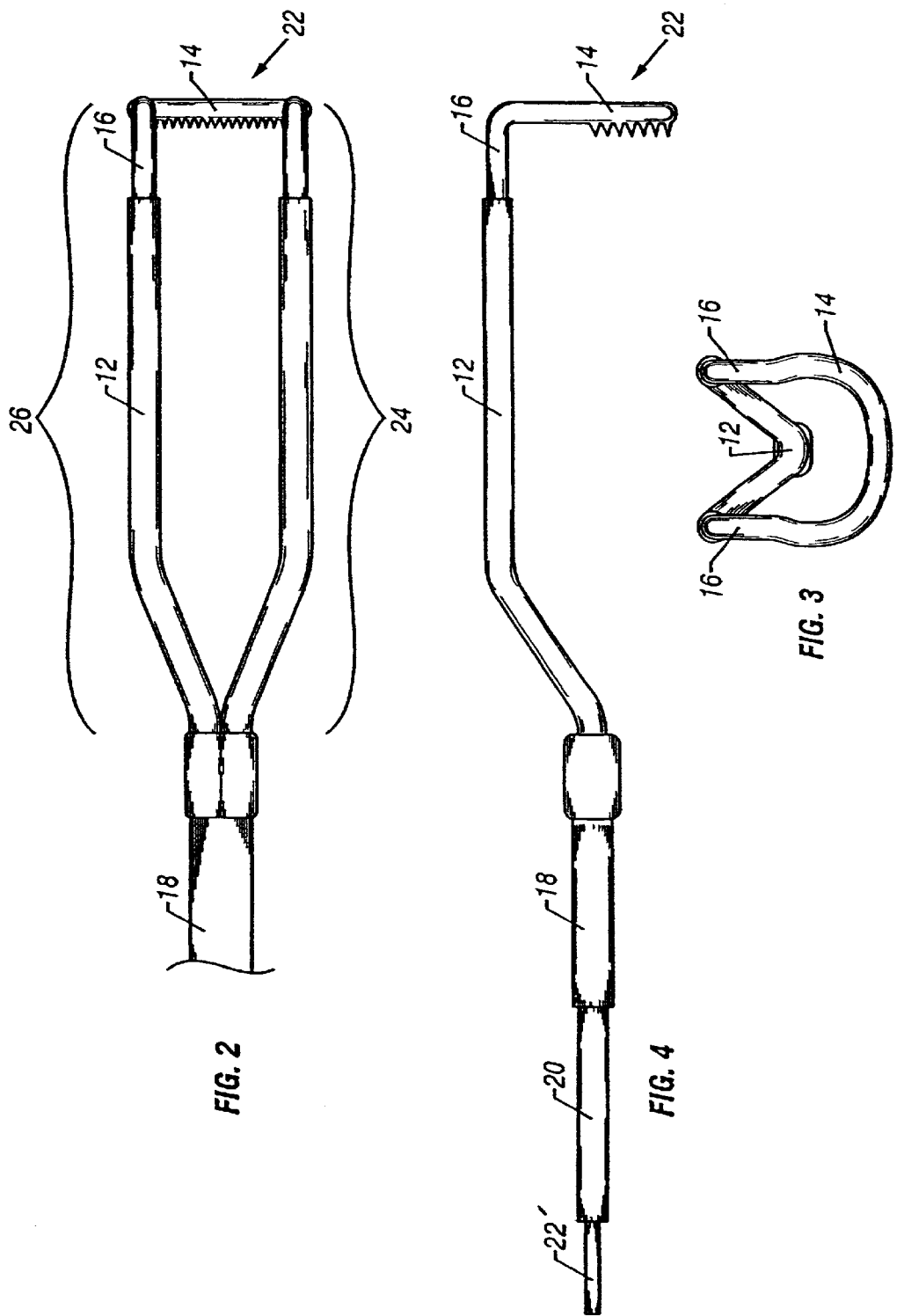

INSULATED ELECTRODE AND METHOD OF ASSEMBLY

FIELD OF THE INVENTION

The present invention relates to an insulated electrode used during surgical procedures and a method of assembling an insulated electrode. The present invention particularly relates to electrode insulators and methods of insulating an electrode that reduce meltback of the insulation and the incidence of scope damage due to high temperatures generated during the cutting or coagulation cycle.

BACKGROUND OF THE INVENTION

Resectoscopes are commonly used to cut and coagulate tissue of a patient during a surgical procedure. The typical resectoscope includes an optical component for illuminating and viewing a target tissue, valves for controlling irrigating fluids, an active element, such as a loop electrode, for cutting tissue and sealing blood vessels, and a handle assembly for connecting electrosurgical current from a generator to the loop electrode. During the surgical procedure, radio frequency (RF) electrical energy passes through the electrode, into the target tissue and causes heating of the target tissue. The amount of heat applied to the tissue controls the cutting and coagulation process.

An example of a surgical procedure utilizing a resectoscope is transurethral resection of the prostate (TURP). TURP is used to treat benign prostatic hyperplasia (BPH), a medical condition causing urinary tract obstruction commonly experienced by men over fifty years old. During the surgical procedure, the surgeon uses a loop electrode to remove the obstructing tissue one piece at a time. Tissue pieces are washed into the bladder using irrigating fluids and subsequently flushed out at the end of the procedure. Various instruments for performing surgical cutting and coagulation procedures such as TURP are known in the art.

An example of such a device may be found in U.S. Pat. No. 5,658,280, which discloses an electrode assembly for a resectoscope. The electrode assembly includes a cutting electrode and a coagulation electrode, with insulation surrounding at least a portion of both the cutting and coagulation electrodes. A support frame connects the cutting and coagulation electrodes to an energy source for supplying energy to the electrodes. The coagulation electrode provides tissue coagulation simultaneously while the cutting electrode cuts tissue.

A further example may be found in U.S. Pat. No. 5,702,387, which discloses an electrosurgical electrode which resists buildup of eschar. The electrode includes a coating of silicone elastomer, applied by dipping, molding or electrostatically spraying the silicone onto the electrode, which improves the ease of cleaning any tissue buildup, such as eschar. The coating is thin or nonexistent at the electrode blade edges and tip. A function of this particular silicone coating configuration is to concentrate the current at the edges and tip of the electrode, resulting in improved eschar removal.

Yet still a further example is found in U.S. Pat. No. 5,810,764, which discloses an electrosurgical probe with an active electrode coupled to a high frequency voltage source. In one aspect of the invention, the active electrode includes a "non-active" portion or surface that selectively reduces undesirable current flow from the non-active portion into tissue or surrounding electrically conducting liquids. The "non-active" electrode portion is coated with an electrically insulating material which is applied to the electrode by plasma deposition, evaporative or sputtering techniques, or dip coating processes.

The above-described electrodes used. during an electrosurgical procedure (and other similar devices not specifically described) offer many advantages to potential users, including effectiveness, safety and convenience. However, it has been discovered that an obstacle or disadvantage to such devices is the susceptibility to meltback of currently used insulation materials and insulation designs. This is due to a variety of factors, including high temperatures generated during the cutting cycle. When the insulation is compromised due to meltback, there is the likelihood that the adjoining components of the resectoscope may also be damaged by the high temperatures. Further, the additional exposed surface area of the active portion of the electrode may destroy surrounding non-target tissue and cause patient injury.

There are a number of causes of current meltback problems. For example, insulators made from Fluoronated Ethylene Propylene (FEP) or Tetra Fluoro Ethylene (TFE) do not closely conform to the external diameter of the electrode wire and therefore lead to concentrated contact points which, due to the somewhat low melting point of FEP and TFE, makes. these contact points more susceptible to meltdown. In addition, the insulators such as sputtered silicone coatings similarly do not provide the uniformity of insulation, thus leading to uneven heat concentration. Moreover, the sputtering process is expensive and difficult to perform reliably.

In view of the above, it is apparent that there is a need to provide an electrode such as those described above with a more durable and reliable insulation element and insulator design that can withstand the range of temperatures generated during an electrosurgical procedure. There is also a need to provide a method of manufacturing such an improved insulator that is efficient, easy to implement and cost effective. Such insulation characteristics include electrical insulation resistance to meltback and efficient manufacturability to ensure the device is biocompatible and non-toxic so as to prevent adverse reactions in both patients and users of the device. It further includes properties that reduce the incidence of scope damage caused by electrical discharge and the intensity of heat generated during the cutting and coagulation cycles.

OBJECTS AND SUMMARY OF THE INVENTION

In view of the foregoing, it is an object of the present invention to provide an insulated electrode assembly that addresses the. obstacles and disadvantages associated with the current problems of insulation meltback and inadvertent electrical discharge due to a variety of factors, including generation of high temperatures and arcing to the resectoscope during surgical procedures.

A further object of the present invention is to provide an insulated electrode assembly that reduces the incidence of scope damage due to the high temperatures generated during cutting and coagulation cycles and inadvertent electrical discharge caused by arcing to the resectoscope.

A further object of the present invention is to provide an insulated electrode assembly that reduces insulation meltback caused by high heat intensities.

A further object of the present invention is to provide an insulated electrode assembly that prevents the destruction of surrounding non-target tissue and reduces potential patient injury.

A further object of the present invention is to provide an insulated electrode assembly that includes uniform insulation thickness and surface contact between the insulation and the electrode.

These and other objects not specifically enumerated herein are believed to be addressed by the present invention which contemplates an electrode assembly that includes an elongated wire and an insulation tube located on a portion of the wire, wherein the insulation tube in an undeformed state may have an internal diameter smaller than the external diameter of the elongated wire. The insulation tube or element that is disposed on the active portion of the electrode forms a non-active section.

The present invention also contemplates a method of assembling insulation onto an electrode which may include the steps of sliding one end of an insulation tube over an assembly tool tip and securing the insulation tube to the tool. The next steps may include positioning one end of the electrode into the other end of the insulation tube and introducing a flow of fluid through the insulation tube. The following step would include inserting the electrode into the insulation tube during the flow of fluid causing the insulation tube to float over the electrode. The final step would likely include discontinuing the flow of fluid so that the insulation surface uniformly contacts the electrode.

BRIEF DESCRIPTION OF THE DRAWINGS

Other features and advantages of the present invention will be seen as the following description of particular embodiments progresses in conjunction with the drawings, in which:

FIG. 2 is a top perspective view of a portion of an electrode assembly in accordance with the present invention;

FIG. 3 is a front perspective view of an electrode assembly in accordance with the present invention;

FIG. 4 is a side perspective view of an electrode assembly in accordance with the present invention;

DETAILED DESCRIPTION OF THE INVENTION

Figure 1:
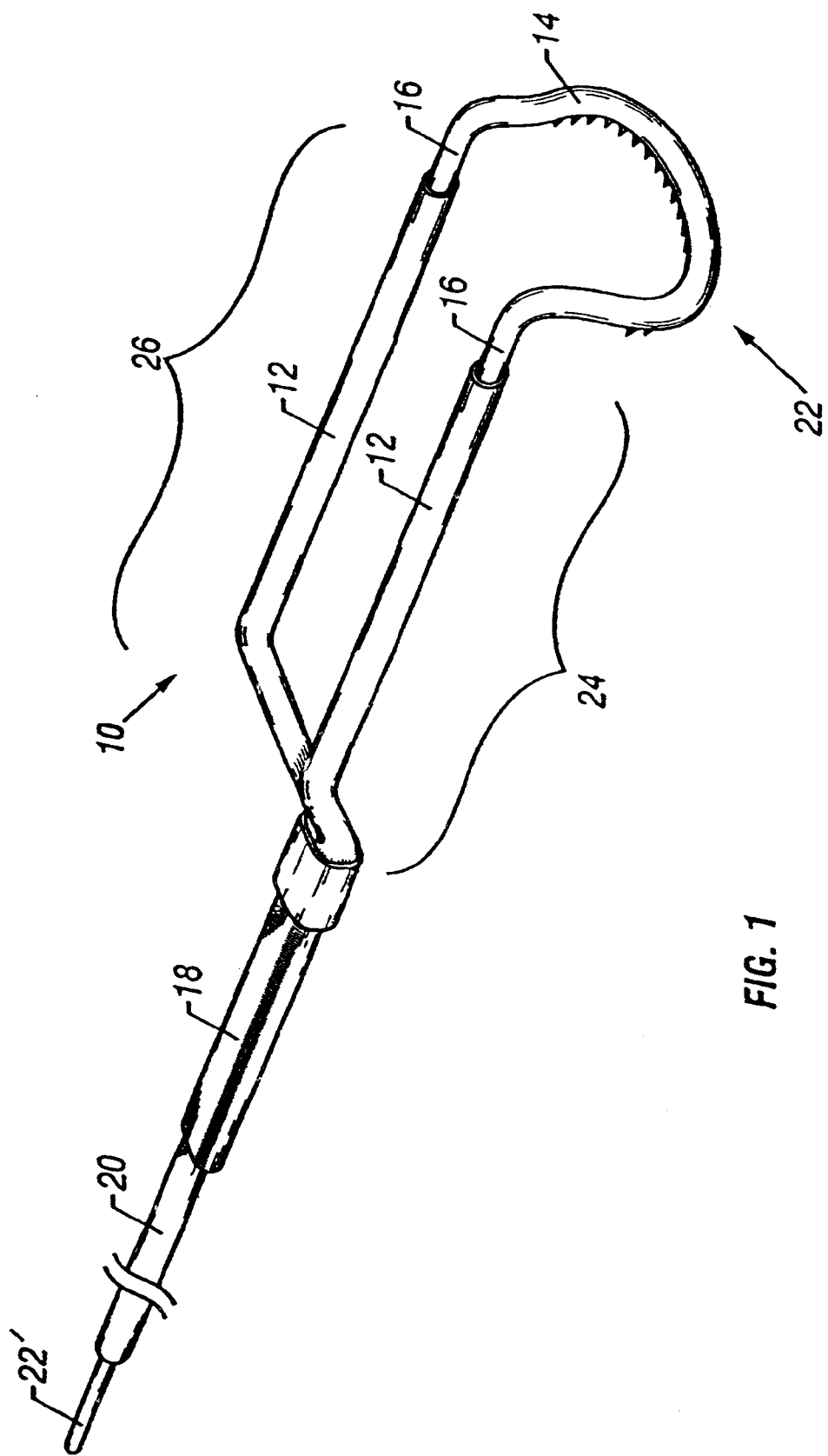
FIG. 1 is a perspective view of an electrode assembly in accordance with the present invention.

Referring to FIG. 1, an embodiment of an electrode assembly 10 for use with a resectoscope or other similar device in accordance with the present invention includes a support tube 12 and an active element 14 for cutting tissue and sealing blood vessels. A portion of the distal end of the active element 14 is surrounded by an insulation tube 16. The insulation tube 16 is non-active and protects adjacent tissues and blood vessels. Additionally, the non-active insulation tube 16 allows the surgeon to selectively cut and coagulate tissue only at the target site. An outer tube 18 and a stem tube 20 are located along a segment of the electrode assembly 10. The outer tube 18 provides structural support for the electrode assembly 10 when affixed to a resectoscope or similar device. The stem tube 20 provides a layer of insulation for the active element 16 as it extends along the length of the electrode assembly 10. A power contact 22' attached to the proximal end of the active element 14 electrically couples the active element 14 to a power supply (not shown) to provide power to the electrode assembly 10.

In a preferred embodiment, the distal end of the active element 14 has a loop geometry as shown in FIGS. 1, 2 and 3. Appropriate active element 14 geometries include, but are not limited to, radial, circular, elliptical, curved, rounded, bowed, arc, arch, crescent, semicircle, malleable, roller cylinder and roller ball. When configured in a loop geometry, the active element 14 has a preferred loop diameter of approximately 24 French (8 mm). However, the loop diameter of the active element 14 can range from 22 to 28 French (7.33 to 9.33 mm), or any suitable size that enables the electrode assembly 10 to fit into a resectoscope or similar device. Further, when configured in a loop geometry, the distal end of the active element 10 forms a pair of spaced semi-parallel arm sections 24, 26 which angle forwardly and upwardly and are connected by the loop.

The active element 14 is typically a wire that transfers energy from a generator or power. source (not shown) to. a tissue target area. The cross-sectional outline of the active element 14 may encompass a variety of shapes including, but not limited to, circular, oval, rectangular, square, triangular, C-shaped or combinations of the above. In addition, in a preferred embodiment, the cross-sectional diameter of the active element 14 is approximately 0.51 mm (0.020 in).

As shown in FIGS. 1, 2 and 4, the distal end 22 of the active element 14 can include grooves or slots of a variety of shapes that promote high electric field intensities and enhance tissue cutting capabilities of the active element 16. A variety of electrical conductive materials maybe used to fabricate the active element 14. These material's include, but are not limited to, tungsten, its alloys, stainless steel and the like. A preferred material is Molybdenum.

Figure 5:
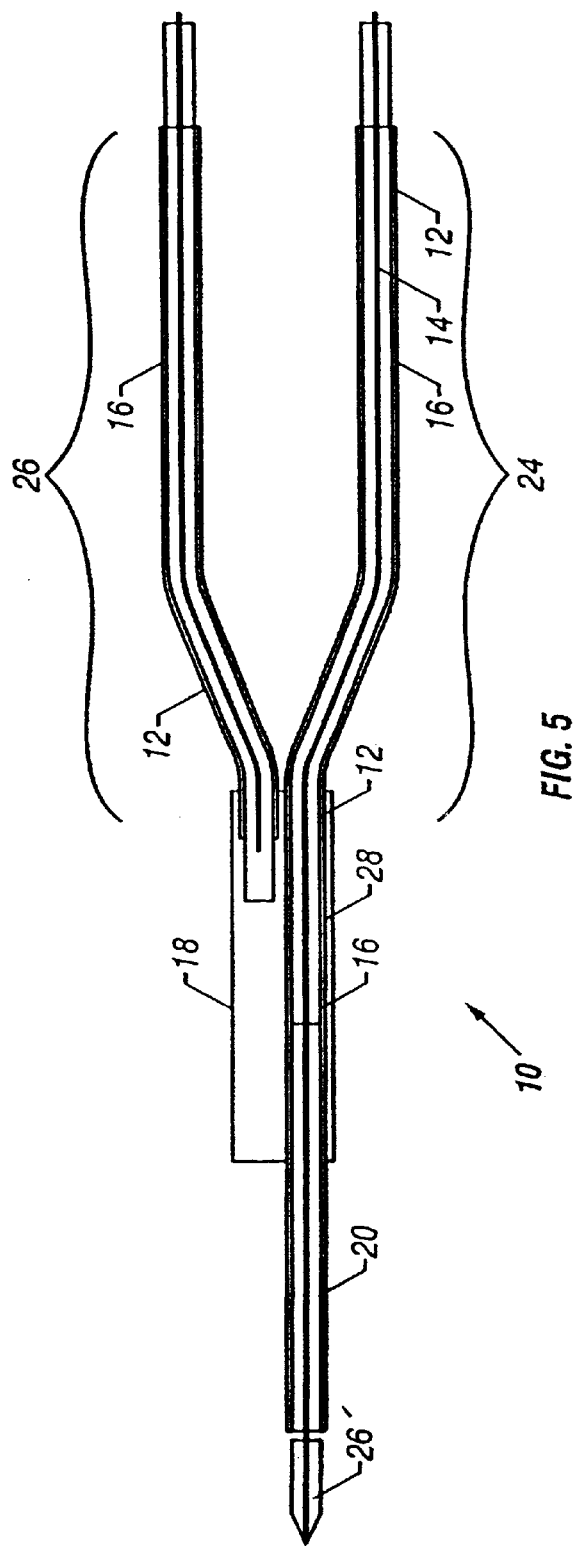
FIG. 5 is a cross-sectional top view of an electrode assembly in accordance with the present invention.

As shown in FIG. 5, the electrode assembly 10 further includes an insulation tube 16 that extends along and shields a. portion of the active element 14. For the electrode assembly 10 shown in FIG. 5, two separate sections of insulation tube 16 are, required to adequately surround the active element 14 of the electrode assembly 10. In a preferred embodiment, the insulation tube 16 is made of a non-active, elastic electrical insulation material, such as silicone, that is capable of being easily stretched or expanded and resuming its former shape. The preferred insulation material is silicone because of its good electrically insulating properties, biocompatibility and high melting point and it conforms very well to mating surfaces.

Figure 6:
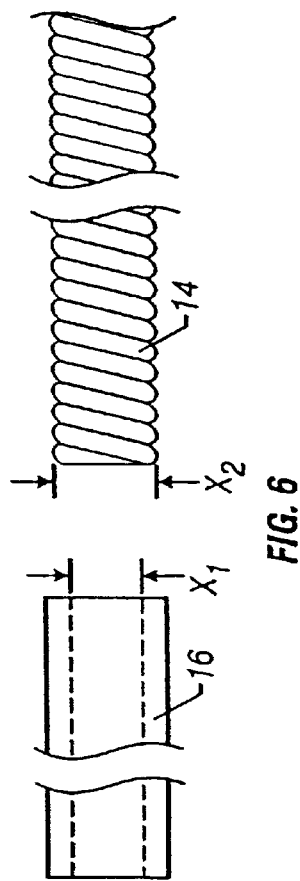
FIG. 6 is a cross-sectional side view of an insulation tube, illustrating its inner diameter, and a wire element, illustrating its outer diameter, in accordance with the present invention.

Referring to FIG. 6, preferably in its unmounted or undeformed state, the inner diameter of the insulation tube 16 is either less than or very nearly equal to the outer diameter of the active element 14. This relative sizing of the tube 16 to the active element 14 ensures that there is a snug and conforming fit and contact between the tube 16 and the element 14, particularly in view of the elastically stretchable and expandable properties of the insulation tube 16. It also enables the use of an insulation tube of maximum thickness thus ensuring that the dielectric strength and the insulating properties of the device are maximized. In this connection, it is desired that the tube material be in tension, even if it is minimal tension, when the tube 16 is mounted on the element 14. This desirable configuration is achieved when the diameter of the tube 16 is either less than or very nearly equal to the outer diameter of the active element.

In a preferred embodiment of the invention, the insulation tube 16 has a manufacturing specification of 0.5080 mm+/−0.0508 mm (0.020 in +/−0.002 in) for its inner diameter and 0.9906 mm+/−0.0508 mm (0.039 in+/−0.002 in) for its outside diameter and the active element 14 has a manufacturing specification of 0.5080 mm+/−0.0203 mm (0.020 in +/−0.0008 in) for its outside diameter. An insulation tube 16 and an active element 14 manufactured according to these specifications achieves the aforedescribed mounting characteristics of the insulation tube 16.

Another aspect of the insulation tube 16 that is advantageous to achieving the goals of the invention is the use of a material that has a high coefficient of friction relative to the metal comprising the active. element 14. The use of such a material better ensures secure and conforming mounting and adherence of the tube 16 to the element 14. In a preferred embodiment, the insulation tube 16 is made of silicone which has a coefficient of friction against a steel or Molybdenum surface of approximately 0.80 (dry). This may be contrasted with conventional insulation materials such as FEP or TFE, which typically have a lower coefficient of friction, such as 0.04 (dry).

The improved uniform surface contact achieved by the present invention, especially at the junction where the active element 14 is exposed from the insulation tube 16 at the distal end of the electrode assembly 10, reduces the potential for tissue to adhere to the junction or fluid to wick between the insulation tube 16 and the active element 14. It also better ensures uniform absorption of heat generated by the active element 14 thereby minimizing potential damage to surrounding tissues.

The outer surface of the insulation tube 16 is relatively smooth. In addition, the thickness of the insulation tube 16 is uniform along its entire length so as to adequately protect and shield the active element 14. However, in an alternate embodiment, the thickness of the insulation tube 16 may be variable along its length depending on various desired electrical insulation characteristics or assembly constraints.

Referring to FIGS. 1 and 5, additional elements comprising the electrode assembly 10 include a support tube 12, stem tube 20, stiffener sleeve 28, outer tube 18 and power contact 22' (FIG. 1) or 26' (FIG. 5). A support tube 12 circumscribes and extends along each arm section 24, 26 of the electrode assembly 10 to provide sufficient rigidity and structural support to the underlying sections of the active element 14 and insulation tube 16. In a preferred embodiment, the support tube 12 is made of stainless steel, however other comparable materials which are corrosion resistant and easily formed, soldered and cleaned may also be used.

Surrounding the proximal section of the active element 14 and providing additional strength and durability is a non-conductive stem tube 20. In a preferred embodiment, the stem tube 20 is made from FEP. Alternatively, the stem tube 20 may be fabricated from other materials such as TFE or Polyethylene. A stiffener sleeve 28 extends substantially along a portion of the insulation tube 16 and the entire length of the stem tube 20, abutting the proximal end of the support tube 12 located on one arm section 24 of the electrode assembly 10. The stiffener sleeve 28 insulates and seals a portion of the electrode assembly 10, facilitating connection of the electrode assembly 10 into a resectoscope.

As shown in FIG. 5, an outer tube 18 is used to secure the proximal ends of the arm sections 24, 26 and provide additional structural support for the electrode assembly 10. The outer tube 18, like the support tube 12, can be made of stainless steel or a similar corrosion resistant material. The distal end of the outer tube 18 is secured to the support tube 12 by soldering the support tube 12 into the outer tube 18. The proximal end of the outer tube 18 is contained within a crimp so an edge is not created between the outer tube 18 and the stem tube 20.

Located at the proximal end of the electrode assembly 10 is a power contact 26'. The power contact 26' couples the active element 14 to a power supply to provide power to the electrode assembly 10. The power contact 26' is an electrically-conductive element formed from stainless steel or some other suitable conductive metal.

It should be understood that the invention is not limited to electrode assemblies comprising an active element that connects to a single power contact. For example, the active element may have two or more ends or terminals extending equal in length to the proximal end of the electrode assembly. Further, two or more power contacts may be used to connect the electrode assembly to the power source.

The electrode assembly 10 of the present invention can be used in both monopolar and bipolar devices. A monopolar device, as described above, directs electric current along a defined path from the exposed active element 14 of the electrode assembly 10 (i.e. the cutting electrode) through the patient's body and to a return electrode (not shown). The return electrode is externally attached to an appropriate area on the patient's body.

A bipolar device includes both the cutting electrode and return electrode on the same device. The cutting electrode and return electrode are configured adjacent to each other so that they simultaneously contact tissue, thereby directing current to flow along a path from the cutting electrode through the patient's tissue and to the return electrode. A portion of the return electrode in a bipolar device of the present invention is insulated, similar to the configuration of the insulation tube 16 located on the active element 14. Preferably; the insulation is made of silicone, but other comparable materials previously described can also be used. The insulation, provides a layer of protection for surrounding tissues and aids in focusing the electric current on target tissues.

Method of Assembly

Figure 7:
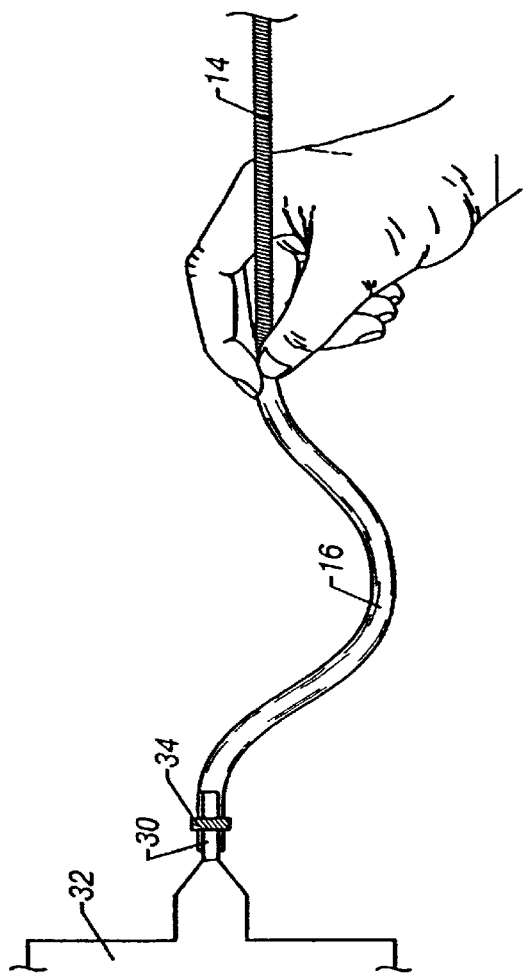
FIG. 7 is a perspective view of a method of positioning one end of a wire element adjacent to one end of an insulation tube.
Figure 8:
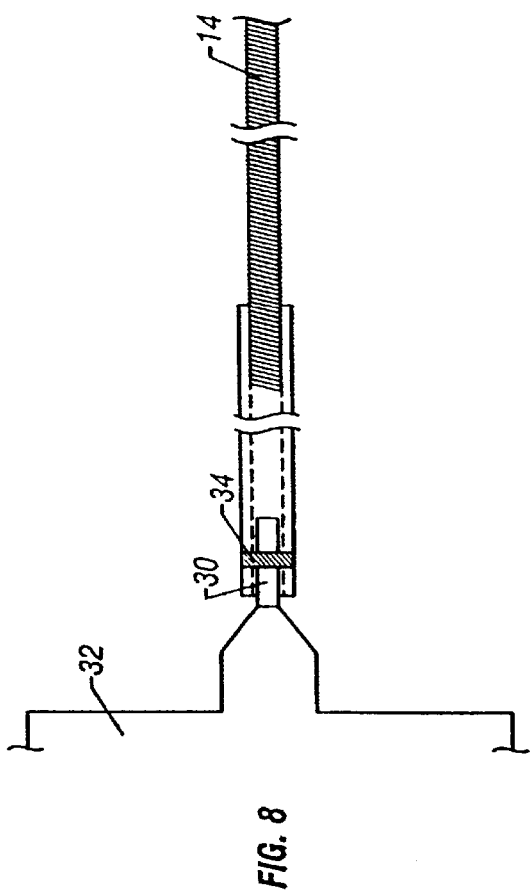
FIG. 8 is a perspective view of a method of inserting a wire element into an insulation tube.

The present invention also contemplates a method of assembling the insulation tube 16 onto the active element 14 of the electrode assembly 10, as shown in FIGS. 7 and 8. The first step of assembling the insulation tube 16 onto the active element 14 includes attaching one end of the insulation tube 16 to an appropriately sized needle 30 of a pressurized fluid source 32. Although a preferred embodiment of the present invention utilizes a pressurized fluid source 32, similar fluid compression devices may be substituted. A variety of fluids used with these devices include, but are not limited to, air, liquid and gas. The pressure regulator (not shown) of the pressurized fluid source 32 is set to 100 psi. It should be noted that alternative pressures may be used dependent upon the durometer, tensile strength and other material characteristics of the insulation tube 16.

The next steps involve securing the insulation tube 16 onto the needle 30 of the pressurized fluid source 32 and positioning one non-loop end of the active element 14 in the open end of the insulation tube 16. A clip 34 or other similar attachment device can be used to secure the insulation tube 16 onto the needle 30. The attachment device should sufficiently clamp the insulation tube 16 to prevent the insulation tube 16 from slipping off the needle 30 when fluid is introduced.

The following steps include introducing fluid into the insulation tube 16 and inserting the active element 14 into the insulation tube 16. Due to the insulating material's high coefficient of friction and its inner diameter relative to the outer diameter of the active element 14, the insulation tube 16 cannot simply slide over the active element 14. Therefore, fluid is slowly introduced into the insulation tube 16 via the needle 30. of the pressurized fluid source 32. As fluid-flows through the insulation tube 16 the pressure causes the insulation tube 16 to expand in a radially outwardly direction. As a result, the inner diameter of the insulation tube 16 increases in size. When the inner diameter of the insulation tube 16 becomes sufficiently greater than the outer diameter of the active element 14, the active element 14 is inserted into the insulation tube 16 until the insulation tube 16 is tight against the loop of the active element 14.

The final assembly step would likely include discontinuing the flow of fluid so that the inner surface of the insulation tube 16 uniformly contacts the outer surface of the active element 14. Due to the elastomeric properties of the insulation tube 16, the diameter and shape of the insulation tube 16 return to a configuration constrained only by the shape of the now-inserted wire when fluid no longer flows through the insulation tube 16. That is, since the original inner diameter of the insulation tube 16 may be smaller than the outer diameter of the active element 14, the inner surface of the insulation tube 16 uniformly contacts the outer surface of the active element 14.

An alternate method of assembly includes soaking the insulation tube in freon, acetone, xylene and the like. Over a period of time, these chemicals permeate and subsequently expand the structure of the insulation tube 16. When the insulation tube 16 is in this expanded state, the active element 14 may be manually inserted into the insulation tube 16. After the insulation tube 16 is positioned on the active element 14, the structure of the insulation tube 16 will revert to its original configuration when the chemicals naturally vaporize out of the insulation tube 16.

Various processes well known in the art may be used to enhance the elastomeric properties of the insulation tube 16 prior to its assembly onto the active element 14. The material properties of the insulation tube 16 can be enhanced via a post-cure process after the material has been extruded. The post-cure process involves the steps of positioning various lengths of insulation tube 16 into a stainless steel pan and placing them into an oven or similar device set at an appropriate temperature for a suitable length of time. In the preferred embodiment, the oven is set at 166° C.±5° C. and the post-cure continues for a duration of approximately 2 to 3 hours. However, based upon the material type, the post cure process may be performed at various temperatures and time durations.

Another aspect of the present invention involves the addition of colorant to the material that comprises the insulation tube 16. As a convenience to the user, colorant is added to the insulation tube 16 material prior to performing the extrusion process. Each of the various colors of insulation tube corresponds to a unique loop size of the active element 14. For example, a yellow insulation tube 16 corresponds to a 24 French size loop, likewise a white insulation tube 16 corresponds to a 26 French size loop, and so on. This aids the user of the device in easily and conveniently selecting the appropriate loop size of the active element 14 for the particular procedure to be performed.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of insulating a wire element of a surgical electrode device comprising the steps of:

providing an uninflated silicone tube of a material suitable for incorporation in a surgical electrode device;

sliding one end of the uninflated silicone tube over an assembly tool tip;

securing said uninflated silicone tube to said assembly tool tip;

positioning an end of the wire element in a second open end of said uninflated silicone tube;

inflating said silicone tube with a flow of fluid through said assembly tool tip;

directing said wire element into said silicone tube; and discontinuing said flow of fluid so that said silicone tube sheaths said wire element.

2. The method of claim 1 wherein a fluid flows through said assembly tool to inflate said silicone tube.

3. The method of claim 1 wherein a clip is used to secure said silicone tube to said assembly tool tip.

4. The method of claim 1 wherein inflating said silicone tube includes expanding said silicone tube in a radially outwardly direction, and wherein the wire element is provided with an external diameter greater than an internal diameter of said silicone tube.

5. The method of claim 1 wherein said internal diameter of said silicon tube is nearly equal to the external diameter of said wire element.

6. The method of claim 5 wherein said coefficient of friction of said silicone tube against said wire element is approximately 0.8.

7. The method of claim 1 wherein directing said wire element includes locating said second end of said silicone tube adjacent to a loop proximally located on said wire element.

8. The method of claim 1 further comprising deflating said silicone tube.

9. The method of claim 8 wherein an internal surface of said silicone tube uniformly contacts and external surface of said wire element.

10. The method of claim 1 wherein introducing a flow of fluid includes expanding said elastomeric tube in a radially outward direction, and wherein the wire element is provided with an external diameter greater than an internal diameter of said elastomeric tube.

11. A method of insulating a wire element of a surgical cutting and coagulation electrode device, the method comprising the steps of:

providing an elongated elastomeric uninflated tube constructed of a material that is suitable for incorporation in the surgical device;

introducing a flow of fluid through said uninflated tube;

moving said wire element into said tube during said flow of fluid; and, discontinuing said flow of fluid so that said tube sheaths said wire element.

12. The method of claim 11 wherein said elastomeric tube is made of silicone.

13. The method of claim 11 wherein said fluid is air.

14. The method of claim 11 further comprising attaching one end of said elastomeric tube to a needle of a pressurized fluid source.

15. The method of claim 14 further comprising attaching a clip to secure said elastomeric tube to said needle of said pressurized fluid source.

16. The method of claim 15 further comprising adjusting a regulator of said pressurized fluid source to 100 psi.

17. The method of claim 14 further comprising positioning one end of said wire element adjacent to another open end of said elastomeric tube.

18. The method of claim 17 wherein after moving said wire element the act of inserting said wire element into said elastomeric tube until a second end of said elastomeric tube abuts a loop proximally located on said wire element.

19. The method of claim 11 further comprising sheathing said wire element in said elastomeric tube.

20. The method of claim 19 wherein an internal surface of said elastomeric tube uniformly contacts an external surface of said wire element.

* * * * *